United States Patent
Furuta et al.

(10) Patent No.: US 6,710,176 B2
(45) Date of Patent: Mar. 23, 2004

(54) PROCESS FOR PRODUCING WATER-SOLUBLE POLYSACCHARIDES, AND METHOD FOR CLARIFYING WATER-SOLUBLE POLYSACCHARIDE AQUEOUS SOLUTIONS

(75) Inventors: Hitoshi Furuta, Ibaraki (JP); Taro Takahashi, Ibaraki (JP); Ryosuke Kiwata, Ibaraki (JP); Akihiro Nakamura, Izumisano (JP); Hirokazu Maeda, Izumisano (JP)

(73) Assignee: Fuji Oil Co., LTD, Osaka (JP)

( * ) Notice: Subject to any disclaimer, the term of this patent is extended or adjusted under 35 U.S.C. 154(b) by 45 days.

(21) Appl. No.: 09/792,896

(22) Filed: Feb. 26, 2001

(65) Prior Publication Data

US 2001/0034443 A1 Oct. 25, 2001

(30) Foreign Application Priority Data

Mar. 14, 2000 (JP) ........................................ 2000-070188

(51) Int. Cl.$^7$ ................................................ C07H 1/00
(52) U.S. Cl. ...................................... 536/123.1; 435/99
(58) Field of Search ........................... 536/123.1; 435/99

(56) References Cited

U.S. PATENT DOCUMENTS 5,112,964 A    5/1992   Aoe et al.

FOREIGN PATENT DOCUMENTS

| EP | 0 598 920    | 6/1994  |
|----|--------------|---------|
| JP | A 3-236759   | 10/1991 |
| JP | A 7-188301   | 6/1995  |
| JP | 07188301     | 7/1995  |
| JP | 11240902     | 9/1999  |
| JP | A 11-240902  | 9/1999  |
| WO | WO 91/00027  | 1/1991  |

*Primary Examiner*—Phyllis G. Spivack
*Assistant Examiner*—C. Delacroix-Muirheid
(74) *Attorney, Agent, or Firm*—Paul & Paul

(57) ABSTRACT

By amylase treatment of water-soluble polysaccharide aqueous solutions extracted from legumes under acidic conditions, for hydrolysis of the starch substances that are a source of precipitates and suspended matter, it is possible to improve the clarity of the aqueous solutions while also preventing production of precipitates during long-term storage or cold storage of the aqueous solutions.

10 Claims, No Drawings

US 6,710,176 B2

PROCESS FOR PRODUCING WATER-SOLUBLE POLYSACCHARIDES, AND METHOD FOR CLARIFYING WATER-SOLUBLE POLYSACCHARIDE AQUEOUS SOLUTIONS

BACKGROUND OF THE INVENTION

1. Field of the Invention

The present invention relates to a process for producing water-soluble polysaccharides, and to a method for clarifying water-soluble polysaccharide aqueous solutions and, more specifically, it relates to a process for efficiently and conveniently producing and clarifying water-soluble polysaccharides derived from legumes, which gives visible transparency and clarity with no turbidity or precipitate production even after long-term storage or cold storage of aqueous solutions of the extracted water-soluble polysaccharides, and which results in a lower degree of browning or moisture absorption with long-term storage.

2. Description of the Related Art

The present inventors have already filed Japanese Patent Application No. 2-30677 (Japanese Unexamined Patent Publication No. 3-236759) based on the discovery that when extracting water-soluble polysaccharides from legumes such as soybeans or green peas which contain abundant protein components, extraction at a pH near the isoelectric point of the protein components contained in the legumes hampers elution of the abundantly present protein components in the legumes, thus facilitating the subsequent purification step.

The present inventions have also already filed Japanese Patent Application No. 5-329214 (Japanese Unexamined Patent Publication No. 7-188301) for a method of hydrolyzing and solubilizing the suspended protein components for the purpose of improving the clarity of the water-soluble polysaccharides obtained by the aforementioned method, and Japanese Patent Application No. 10-43756 (Japanese Unexamined Patent Publication No. 11-240902) for a method of promoting production of, and removing, the suspended matter by concentration during the production steps. The aqueous solutions of water-soluble polysaccharides prepared by these methods have dramatically improved clarity, but a problem has remained in that the water-soluble polysaccharides dissolve in the aqueous solutions, and water-insoluble suspended substances or precipitates are produced with long-term storage or cold storage.

These suspended substances or precipitates have been very difficult to remove industrially because they are produced after long-term storage or cold storage. In particular, when a water-soluble polysaccharide is cooled after preparation or the water-soluble polysaccharide is heated to form an aqueous solution and then placed in cold storage, the resulting colloidal suspended substances have been difficult to remove, and the colloidal suspended substances have been a cause of clogging of filters or columns in the UF apparatuses or the like which are used in a cooled state during production of the water-soluble polysaccharide.

As means for solving this problem there have been known, in addition to the method of protein component hydrolysis of the aforementioned prior application, also precipitation and removal of suspended substances using a centrifugal separator with a high centrifugal force, and removal of suspended substances and precipitates using filters with small pore sizes or filter aids such as diatomaceous earth. When high centrifugal force is used, however, the high cost of the equipment poses a problem in terms of production. When various filters are used, the high viscosity of the suspended substances has tended to result in clogging which prevents any extended treatment. Thus, it has been difficult to efficiently remove peptide components that are products of low molecular weight conversion with proteases and cause browning or moisture absorption after drying, and such browning has therefore not been preventable.

The water-insoluble suspended substances or precipitates produced after storage of water-soluble polysaccharides obtained by extraction from legumes in the manner described above are believed to consist mostly of insoluble protein components, insoluble salts and portions of the micronized starting material, while the sugar components in particular are believed to consist of difficult-to-separate hemicelluloses and celluloses. It is therefore thought that hydrolysis of these polysaccharide components with enzymes such as hemicellulases and cellulases results in hydrolysis of the useful water-soluble polysaccharide components as well, making it impossible to obtain the desired water-soluble polysaccharides.

In the case of legumes that contain abundant amounts of starch components, such as green peas and red beans, the possibility of elution of the starch components into the extracted water-soluble polysaccharide fraction had been amply considered, but in the case of soybeans which are a more useful source for water-soluble polysaccharide extraction, the starch component content in mature soybeans is considered to be very low, and therefore the starch components in the extracted water-soluble polysaccharides have not received much attention nor been studied.

BRIEF SUMMARY OF THE INVENTION

It is an object of the present invention to efficiently produce water-soluble polysaccharides whose aqueous solutions have low turbidity and little production of suspended substances or precipitates even during long-term storage or cold storage, and which exhibit minimal browning and moisture absorption during long-term storage, by a convenient method and from legumes.

As a result of diligent research in light of the circumstances described above, the present inventors have found that a relatively large amount of starch components are present in addition to protein components in the suspended matter produced when extracting and purifying water-soluble polysaccharides from legumes, or when storing water-soluble polysaccharide aqueous solutions after purification. That is, it was found that, even when the starting materials are soybeans, such water-soluble polysaccharide aqueous solutions extracted from the legumes exhibit a violet coloring reaction with iodine solutions which indicates the presence of starch components, and it was conjectured that the suspended substances or precipitates produced upon long-term storage or cold storage of the aqueous solutions are the starch components insolubilized by aging. When such water-soluble polysaccharide aqueous solutions were treated with amylases for hydrolysis of the starch components, it was found that the clarity of the water-soluble polysaccharide aqueous solutions not only improves upon cooling after production, but that production of precipitates during long-term storage and production of suspended substances during cold storage can be prevented. In addition, it was discovered that water-soluble polysaccharides that have been thus treated with amylases cause little clogging of filters used for ultrafiltration (UF) or microfiltration (MF), or membranes of small pore size such as semipermeable membranes and reverse osmosis (RO) membranes, and that when such high efficiency low molecular component removal apparatuses are used in the production of water-soluble polysaccharides, it is possible to more easily produce water-soluble polysaccharides with minimal browning and moisture absorption during storage. The present invention has been completed on the basis of these discoveries.

In other words, the present invention relates to a process for producing water-soluble polysaccharides, which comprises allowing an amylase to act on a water-soluble polysaccharide extract derived from a legume and removing the insoluble matter, and to a method for clarifying a water-soluble polysaccharide aqueous solution, which comprises allowing an amylase to act on a water-soluble polysaccharide extract derived from a legume and removing the insoluble matter.

DETAILED DESCRIPTION OF THE INVENTION

The legumes as used in the invention may be any of various legumes including butter beans, red beans, kidney beans, peas, green peas, cowpeas, horse-beans, soybeans, swordbeans, peanuts, lupins, chick peas, Egyptian kidney beans, mung beans, vetch beans and lentils, as well as various nuts including cashew nuts and the like. When the starting material is soybeans, it may be the okara (bean-curd refuse) obtained as a by-product from preparation of tofu (bean curd) and soybean milk or separated soybean protein.

The starting material may be subjected to thermolytic treatment at a temperature preferably of from 60° C. to 130° C., and more preferably from 80° C. to 130° C., under either acidic or alkali conditions but preferably at an acidic pH of 2–7 and more preferably a pH of 4–7, and most preferably at near the isoelectric point of each protein component, and after separation of the water-soluble fraction, it may be dried directly or subjected to activated carbon treatment, resin adsorption treatment or ethanol precipitation to remove the hydrophobic substances or low molecular substances, and then dried to yield the desired water-soluble polysaccharides. Decomposition extraction may also be carried out with a hemicellulase or pectinase.

According to the invention, the amylase treatment may be carried out during any of the aforementioned steps, or the amylolytic treatment may be carried out after separation of the water-soluble polysaccharides or in an aqueous solution newly prepared after drying.

The conditions for the amylase treatment are not particularly restricted, and the reaction may be conducted under the ideal conditions for the amylase used. In most cases it is more preferably carried out in a high temperature range where the gelatinized state of the starch components can be maintained than a low temperature range. The effect of a heat-resistant amylase will therefore be higher than that of an amylase that exhibits activity only at near room temperature. The treatment can provide an effect even if used at the starting material stage before extraction of the water-soluble polysaccharides.

The amylase may be, for example, a beta-amylase or an alpha-amylase, and such amylases are marketed and readily available and may be used as appropriate. A notable effect can be achieved by combined use with proteases, as described in the aforementioned prior application (Japanese Unexamined Patent Publication No. 7-188301). Whether used alone or in combination with proteases, these amylases will not result in 100% solubilization of the suspended substances, but some will remain as partial insoluble matter. However, the partial insoluble matter has better precipitation and filtration properties than the original material before amylase treatment, and can therefore be easily separated by ordinary centrifugation without high centrifugal force, without tending to clog filtering apparatuses.

Although adequate transparency is achieved simply by removing these suspended substances, it is preferred to remove the low molecular weight amylohydrolysis products or proteohydrolysis products obtained by amylases or proteases to prevent browning of the aqueous solution or dry product during long-term storage and to reduce the hygroscopic property of the dry product in order to increase the range of uses.

The method of removing the low molecular weight substances employed may be ultrafiltration (UF) or microfiltration (MF), a method using a filtering membrane of small pore size such as a semipermeable membrane or reverse osmosis (RO) membrane, a precipitation method using a polar organic solvent such as ethanol, isopropanol or acetone, or an enzyme method using a microorganism, typical of which is alcohol fermentation.

When filtration is employed, ultrafiltration (UF) or microfiltration (MF) or a method using a filtering membrane of small pore size such as a semipermeable membrane or reverse osmosis (RO) membrane may be utilized, having a fractionating molecular weight corresponding to the low molecular weight starch substances produced by the amylase. However, substances exceeding the molecular weight or molecular size of the target water-soluble polysaccharide fraction reduce the yield of the water-soluble polysaccharide, and are unsuitable for purification. The fractionated molecular weight size is usually 1,000 to 5,000,000, and preferably 5,000 to 1,000,000. In a precipitation method using a polar solvent, the concentration will vary depending on the particular solvent, but in the case of ethanol, its concentration may be 30–100%, and preferably 40–90%, as an aqueous solution. If the alcohol concentration is too low, the yield of the water-soluble polysaccharide fraction will be lower, and a higher concentration will lower the purity.

The present invention will now be explained in further detail by way of the following examples and comparative examples which are, however, only exemplary and are not intended to restrict the spirit of the invention in any way. The "parts" and "%" values throughout the examples are all based on weight.

EXAMPLES 1–6

A two-fold amount of water was added to raw okara obtained from the production of separated soybean protein, and extraction was performed under extraction conditions conducive to precipitation during long-term storage, i.e., adjustment to pH 5.0 with hydrochloric acid, and heating at 120° C. for 2 hours. After cooling this to 50° C., centrifugation (10,000 G×30 minutes) was performed and the supernatant and precipitate portions were separated. The polysaccharide extract obtained in this manner was lyophilized once. To a 10% aqueous solution of the water-soluble polysaccharide there were added amylase A (heat-resistant alpha-amylase A3306, product of Sigma Corp.), amylase B (dextrozyme plus L, product of Novo Corp.) and amylase C (Amano AD1, product of Amano Seiyaku Co., Ltd.) at 1% with respect to the water-soluble polysaccharide (in terms of dry weight), and the starches were hydrolyzed under their respective optimum conditions. Specifically, amylase A was reacted at 90° C. for 120 minutes, and amylase B and amylase C were reacted at 50° C. for 120 minutes. After the reaction, each of the solutions was heated for 10 minutes in boiling water and then cooled to room temperature (Examples 1, 2 and 3). After cooling to room temperature, each solution was partially centrifuged at 5,000 G for 10 minutes, and the supernatant liquid was fractioned off (Examples 4, 5 and 6). Next, each solution was diluted to 3% and the turbidity of each solution was measured at OD 610 nm. An iodine solution (solution of 2% KI, 0.2% $I_2$) was added dropwise to each of the solutions to confirm the starch color reaction. The solutions were also allowed to stand at room temperature or 5° C. for 12 hours and the state of precipitate production was observed.

The results are shown in Tables 1 to 4.

COMPARATIVE EXAMPLES 1–4

For comparison the procedure was carried out without using enzymes, and using a protease disclosed in the aforementioned prior application. Specifically, to a 10% aqueous solution of the water-soluble polysaccharide there was added a protease preparation (Actinase AS, product of Kaken Seiyaku Co., Ltd.) at 1% with respect to the solid portion, and reaction was carried out at 50° C. for 120 minutes. The pH was then adjusted to 7 and the mixture was heated in boiling water for 10 minutes to inactivate the enzymes while accomplishing heat treatment, after which it was cooled to room temperature (Comparative Examples 1 and 2). After this treatment, a portion was centrifuged at 5,000 G for 10 minutes in the same manner as the examples, and the supernatant liquid was fractioned off (Comparative Examples 3 and 4). In the same manner as the examples, each solution was diluted to 3% and then the turbidity (OD 610 nm) was measured, and the color reaction against an iodine solution and the production of precipitates were observed.

The results are shown in Tables 1 to 4.

TABLE 1

Turbidity of each treated solution before centrifugation and precipitate production after storage

|  | Comp. Ex. 1 | Comp. Ex. 2 | Example 1 | Example 2 | Example 3 |
|---|---|---|---|---|---|
| Enzyme treatment | No treatment | Protease | Amylase A | Amylase B | Amylase C |
| Turbidity | 0.609 | 0.571 | 0.235 | 0.322 | 0.407 |
| Iodine reaction | + | + | − | − | − |
| Precipitation (room temperature) | ++ | + | − | − | − |
| Precipitation (5° C.) | ++ | ++ | − | − | − |

Note
Iodine reaction: + iodine reaction, − no iodine reaction
Precipitation evaluation: ++ much precipitation, + precipitation, ± little precipitation, − no precipitation

TABLE 2

Turbidity of each treated solution before centrifugation and precipitate production after storage

|  | Comp. Ex. 3 | Comp. Ex. 4 | Example 4 | Example 5 | Example 6 |
|---|---|---|---|---|---|
| Enzyme treatment | No treatment | Protease | Amylase A | Amylase B | Amylase C |
| Turbidity | 0.347 | 0.143 | 0.119 | 0.138 | 0.197 |
| Precipitation (room temperature) | ++ | ± | − | − | − |
| Precipitation (5° C.) | ++ | ± | − | − | − |

Note
Precipitation evaluation: ++ much precipitation, + precipitation, ± little precipitation, − no precipitation

EXAMPLES 7 AND 8

In the same manner as Examples 1 to 6, raw okara obtained from production of separated soybean protein was used as the starting material and a lyophilized water-soluble polysaccharide was prepared. Actinase AS (Kaken Seiyaku Co., Ltd.) was added as the protease and dextrozyme plus L (product of Novo Corp.) was added as the amylase to a 10% aqueous solution of the water-soluble polysaccharide in an amount of 1 wt % with respect to the solid portion of each polysaccharide solution, and reaction was carried out at 50° C. for 120 minutes. After the reaction, the solution was heated for 10 minutes in boiling water and then cooled to room temperature (Example 7). After cooling to room temperature, it was partially centrifuged at 5000 G for 10 minutes, and the supernatant liquid was fractioned off (Example 8). Next, each solution was diluted to 3% and the turbidity of each diluted solution was measured at OD 610 nm. The solutions were also allowed to stand at room temperature or 5° C. for 12 hours and the state of precipitate production was observed.

The results are shown in Tables 3 and 4.

TABLE 3

Turbidity of each treated solution before centrifugation and precipitate production after storage

| | Comp. Ex. 1 | Comp. Ex. 2 | Example 1 | Example 7 |
|---|---|---|---|---|
| Enzyme treatment | No treatment | Protease | Amylase A | Amylase B + Protease |
| Turbidity | 0.609 | 0.571 | 0.235 | 0.117 |
| Precipitation (ordinary temperature) | ++ | + | − | − |
| Precipitation (5° C.) | ++ | + | − | − |

Note
Precipitation evaluation: ++ much precipitation, + precipitation, ± little precipitation, − no precipitation

TABLE 4

Turbidity of each treated solution before centrifugation and precipitate production after storage

| | Comp. Ex. 3 | Comp. Ex. 4 | Example 5 | Example 8 |
|---|---|---|---|---|
| Enzyme treatment | No treatment | Protease | Amylase B | Amylase B + Protease |
| Turbidity | 0.347 | 0.143 | 0.138 | 0.088 |
| Precipitation (room temperature) | ++ | ± | − | − |
| Precipitation (5° C.) | ++ | + | − | − |

Note
Precipitation evaluation: ++ much precipitation, + precipitation, ± little precipitation, − no precipitation These results demonstrate that the combined use of the protease and amylase improved the clarity of the water-soluble polysaccharide, as compared to using the amylase or protease alone.

EXAMPLES 9 AND 10

The water-soluble polysaccharide solutions of Examples 5 and 7 were diluted to 2% aqueous solutions and then subjected to a UF filtration test at 5° C. The test was carried out by fixed concentration treatment using a UF filter with a fractionating molecular weight of 500,000 (Mocellup FB02FUS5081, product of Daicel Chemical Co., Ltd.), supplying ion-exchange water in the same amount as the permeating liquid. The operation was carried out with a liquid permeation pressure of 1.5 atmospheres. The time required for the permeation rate of the permeating liquid to reach ⅔ of that at the start of permeation due to clogging of the UF filter was measured, and this time was recorded as the life of the filter and compared to the result obtained using a non-treated water-soluble polysaccharide solution. Using this UF treatment method, the point at which the permeating liquid volume reached twice that of the original liquid (3-fold concentration) marked the end of the UF treatment, and using treated solutions (purified solutions) only for the examples, they were subjected to a storage test at 70° C. and the spray drying, and the properties of the water-soluble polysaccharides during storage were compared to those before treatment.

The results are shown in Tables 5 and 6.

Comparative Examples 5 and 6

The water-soluble polysaccharide solutions obtained in Comparative Examples 3 and 4 were diluted to 2% and the filter life for each was measured in the same manner as Examples 9 and 10.

The results are shown in Table 5.

TABLE 5

UF treatment of each treated solution and UF filter life

| | Comp. Ex. 5 | Comp. Ex. 6 | Example 9 | Example 10 |
|---|---|---|---|---|
| Enzyme treatment | No treatment | Protease | Amylase B | Amylase B + Protease |
| Filter life | 100 | 172 | 193 | 215 |

Note
The filter life with no enzyme was defined as 100.

TABLE 6

Storage test of UF treated solutions and condition of dry products

| | Solution before UF | | Solution after UF | |
|---|---|---|---|---|
| | Example 9 | Example 10 | Example 9 | Example 10 |
| Browning after storage | + | ++ | − | ± |
| Condition after drying | Strong hygroscopic property | Strong hygroscopic property | Weak hygroscopic property | Weak hygroscopic property |

Note
The conditions after storage and after drying represent the difference as compared with non-UF treatment These results suggest that amylase treatment can extend the life of UF filters compared to the prior art method. In addition, the purified water-soluble polysaccharides from which the low molecular weight components are removed by UF treatment exhibit less browning as compared with unpurified ones, and the dried products have lower hygroscopic properties.

As explained above, by amylase treatment of water-soluble polysaccharide aqueous solutions extracted from legumes under acidic conditions, for hydrolysis and low molecular weight conversion of the starch substances that are a source of precipitates and suspended matter, it is possible to minimize the prior art problems of increased turbidity and production of precipitates occurring with long-term storage or cold storage of water-soluble polysaccharide aqueous solutions, and the result not only gives an enhanced aesthetic quality to the product but also facilitates filtration using filters for ultrafiltration (UF) or microfiltration (MF), or membranes of small pore size such as semipermeable membranes and reverse osmosis (RO) membranes. As a result, it is possible to minimize browning and moisture absorption during long-term storage of water-soluble polysaccharide aqueous solutions or their dried products.

We claim:

1. A production process for producing water-soluble polysaccharides whose aqueous solutions have low turbidity and little production of suspended substances and precipitates even during long-term storage and cold storage, said suspended substances and precipitates being insoluble matter, which process comprises:

allowing an amylase to act on a water-soluble polysaccharide extract derived from soybean, after removing the insoluble mailer, wherein said polysaccharide extract contains starch.

2. A production process according to claim 1, wherein the action of the amylase prevents the starch from exhibiting color reaction when an iodine aqueous solution containing about 2% KI and 0.2% $I_2$ is added dropwise.

3. A production process according to any one of claims 1 or 2, wherein the soybean is okara.

4. A production process according to claim 1, also comprising before the amylase acting step, the steps of:

subjecting soybean to a thermolytic treatment at temperatures from 60–130° C. under either acidic or alkali conditions near the isoelectric point of each protein component thereof;

separating a water-soluble fraction of said thermolytic treated soybean; and removing insoluble matter being hydrophobic substances and low molecular substances from said separated water-soluble fraction.

5. The production process according to claim 4, wherein said amylase acting step is carried out at a high temperature near a gelatinized state of the starch, and wherein after the amylase acting step the water-soluble fraction is dried to yield the water-soluble polysaccharide.

6. The production process according to claim 5, wherein the amylase used in the amylase acting step is selected from the group of alpha-amylase and beta-amylase.

7. The production process according to claim 6, wherein said thermolytic treatment step acidic conditions are in the range of a pH of 4–7 and the temperature range is from 80–130° C.

8. The production process according to claim 5, wherein after the amylase acting step there is a further step of removing the low molecular weight amylohydrolysis products.

9. The production process according to claim 8, wherein the step of removing low molecular weight amylohydrolysis products removes substances exceeding a fractionated molecular weight size of 1,000 to 5,000,000.

10. The production process according to claim 9, wherein the step of removing low molecular weight amylohydrolysis products removes substances exceeding a fractionated molecular weight size of 5,000 to 1,000,000.

* * * * *